(12) United States Patent
Haapakumpu et al.

(10) Patent No.: US 7,294,345 B2
(45) Date of Patent: Nov. 13, 2007

(54) OTORHINOLOGICAL DELIVERY DEVICE

(75) Inventors: Timo Haapakumpu, Littoinen (FI); Harri Jukarainen, Turku (FI); Juha Ala-Sorvari, Turku (FI); Henry Rankonen, Turku (FI); Frederik E. Riphagen, Brussels (BE); Wolfgang Arnold, Munich (DE)

(73) Assignee: Schering Oy, Turku (FI)

( * ) Notice: Subject to any disclaimer, the term of this patent is extended or adjusted under 35 U.S.C. 154(b) by 180 days.

(21) Appl. No.: 10/542,420

(22) PCT Filed: Jan. 14, 2004

(86) PCT No.: PCT/FI2004/000018

§ 371 (c)(1), (2), (4) Date: Jul. 15, 2005

(87) PCT Pub. No.: WO2004/064912

PCT Pub. Date: Aug. 5, 2004

(65) Prior Publication Data

US 2006/0067982 A1 Mar. 30, 2006

(30) Foreign Application Priority Data

Jan. 17, 2003 (EP) .................................. 03000987

(51) Int. Cl.
*A61F 11/00* (2006.01)

(52) U.S. Cl. ...................... 424/434; 128/898; 424/437; 514/953; 523/113

(58) Field of Classification Search .................... None
See application file for complete search history.

(56) References Cited

U.S. PATENT DOCUMENTS

| | | | | |
|---|---|---|---|---|
| 3,710,795 A | * | 1/1973 | Higuchi et al. | 424/424 |
| 3,946,106 A | * | 3/1976 | Chien et al. | 424/425 |
| 3,948,254 A | | 4/1976 | Zaffaroni | 128/127 |
| 3,948,262 A | * | 4/1976 | Zaffaroni | 128/833 |
| 3,993,072 A | * | 11/1976 | Zaffaroni | 424/430 |
| 3,993,073 A | * | 11/1976 | Zaffaroni | 424/424 |
| 4,942,037 A | * | 7/1990 | Bondi et al. | 424/448 |
| 4,959,217 A | * | 9/1990 | Sanders et al. | 424/473 |
| RE35,408 E | | 12/1996 | Petruson | 128/858 |
| 5,980,928 A | | 11/1999 | Terry | 424/427 |
| 6,063,395 A | | 5/2000 | Markkula et al. | 424/422 |
| 6,117,442 A | | 9/2000 | Markkula et al. | 424/422 |
| 6,299,894 B1 | * | 10/2001 | Markkula et al. | 424/422 |
| 6,476,079 B1 | | 11/2002 | Jukarainen et al. | 514/772.4 |

FOREIGN PATENT DOCUMENTS

| | | |
|---|---|---|
| WO | WO 00/00550 | 1/2000 |
| WO | WO 00/29464 | 5/2000 |
| WO | WO 00/33775 | 6/2000 |
| WO | WO 01/85133 | 11/2001 |

\* cited by examiner

*Primary Examiner*—Marc S. Zimmer
(74) *Attorney, Agent, or Firm*—James C. Lydon

(57) ABSTRACT

The invention relates to an otorhinological delivery device comprising at least one pharmaceutically active agent. According to the invention the device comprises a core comprising said at least one pharmaceutically active agent wherein said core is made of an elastomer composition selected from the group consisting of poly(dimethylsiloxane), a siloxane-based elastomer comprising 3,3,3-trifluoropropyl groups attached to the Siatoms of the siloxane units, a siloxane-based elastomer comprising poly(alkylene oxide) groups and mixtures thereof, and a membrane encasing said core, said membrane being made of a same or a different elastomer composition than said core, said elastomer composition being selected from the group consisting of poly (dimethylsiloxane), a siloxane-based elastomer comprising 3,3,3-trifluoropropyl groups attached to the Siatoms of the siloxane units, a siloxane-based elastomer comprising poly (alkylene oxide) groups and mixtures thereof. The invention is characterized in that the pharmaceutically active agent is selected from the group comprising anti-allergic agents, anti-inflammatory agents, anti-fungicides, glucocorticoids and mixtures thereof.

9 Claims, 4 Drawing Sheets

OTORHINOLOGICAL DELIVERY DEVICE

FIELD OF THE INVENTION

This invention relates to an otorhinological delivery device comprising at least one pharmaceutically active agent.

BACKGROUND OF THE INVENTION

The publications and other materials used herein to illuminate the background of the invention, and in particular, the cases to provide additional details respecting the practice, are incorporated by reference. Especially the patents U.S. Pat. No. 6,056,976 and U.S. Pat. No. 6,299,894 as well as the pending applications, U.S. Ser. No. 09/701,547, filed Nov. 30, 2000 (equivalent: WO 00/00550) and WO03/017971 are incorporated by reference.

The concept of treating sudden deafness, Meniere's disease and tinnitus, which are considered to have the same etiology, with corticosteroids applied in the middle ear for perfusion through the round window membrane, has been presented as the future treatment. Sudden deafness has an annual incidence of 2:10 000 and Meniere's disease has an estimated annual incidence of 1:5 000, but because of the chronic nature of this condition, the prevalence figures are much higher. In Germany, about 20 000 patients (on 80 million inhabitants) seek treatment for tinnitus every year, these figures including the severe cases only.

Several publications disclose different devices to be placed in the ear of patients suffering from sudden deafness, Meniere's disease, tinnitus or other ear disorders (such as endolymphatic hydrops, endolymphatic hypertension, perilymphatic hypertension, perilymphatic hydrops, perilymphatic fistula, intracochlear fistula, vertigo, hearing loss related to hair cell or ganglion cell damage or malfunction). Such devices allow the delivery of therapeutic agents to various ear tissues in a controlled manner. For example, a variety of structures have been developed which are capable of delivering therapeutic agents into the external auditory canal of the outer ear or to tissue structures of the inner ear. The same situation exists with tissue materials that lead into the inner ear (e. g. the round window membrane).

Inner ear tissue structures suitable for this kind of treatment comprise the cochlea, the endolymphatic sac/duct and the vestibular labyrinth. Access to these and other inner ear tissue regions is typically achieved through a variety of structures, including but not limited to the round window membrane, the oval window/stapes footplate, the annular ligament, and the otic capsule/temporal bone. Furthermore, the middle ear that is here defined as the physiological air-containing tissue zone behind the tympanic membrane and ahead of the inner ear, may also be used for the delivery of therapeutic agents. One particularity of the ear and the nose, when compared to subcutaneous positioning of delivery devices, is that there are no body fluids that induce and help the release of the active agent and convey it to the target organ.

Corticosteroids are commonly used to treat these diseases. Said devices can be placed in the round window niche or other internal ear cavity.

The U.S. Pat. No. 6,120,484 discloses an otological implant for delivery of a medicament comprising a wick inserted through an aperture in a membrane. One end (distal end) of the wick is in contact with the treatment site and the other end (proximal end) is accessible for contacting with a medicament source. The wick conveys the medicament from the proximal end to the distal end by capillary action. The wick is made for example of polyvinyl acetate, a material that is capable of conveying the medicament by capillary action. The implant may further include a tube member for supporting the wick, said tube being made of silicone, for example. The document does not mention how to regulate the release rate of the medicament.

On the other hand, the patent application WO 00/33775 presents a device for controlled delivery of a therapeutic agent to an internal cavity of the ear. The device is placed so that at least a portion thereof is in the round window niche. The released therapeutic agents come in contact with the round window niche and pass therethrough into the inner ear. The device consists essentially of a carrier media that is combined with said agent. The carrier media may comprise biodegradable material and at least one material of synthetic origin. Said materials may be polymeric materials that are cross-linked and that swell when in contact with water in the body temperature. The application discloses different methods for the release of the agent, such as diffusion, solvent drag, electrodiffusion, osmosis, active/passive transport or a combination thereof. This document discloses that the agent that is positioned deepest in the device, release the slowest. The release rate of the agent thus relates to its relative position within the device, i.e. it relates to the distance to the outer surface of the device.

It is also known from the literature that implants may be used in the nose for controlled delivery of pharmaceutical drugs. An example of such implants is given in the U.S. Pat. No. RE35,408 which presents a metallic nasal drug delivery device comprising end portions in the form of relatively thin tabs. A preferred material for the end portions is silicone rubber (Silastic®). The pharmaceutical drug is contained in surface cavities or pockets or in the coating of the surface.

OBJECTS AND SUMMARY OF THE INVENTION

The object of this invention is to provide an otorhinological delivery device that enables a constant release of one or more pharmaceutically active agents in a manner that does not cause any or minimal discomfort to the patient.

The object of this invention is particularly to provide a delivery device for nasal or otological applications that allows pre-determined, constant release rates of the active agents. A further object of the invention is to provide a delivery device that can be manufactured in a safe and reproducible manner and which manufacturing process's hygiene may be reliably controlled. The invention still aims to provide a delivery device that is safe and easy to introduce into its final position as well as convenient and safe to use.

DETAILED DESCRIPTION OF THE INVENTION

The invention is disclosed in the appended claims.

The otorhinological delivery device comprising at least one pharmaceutically active agent according to the invention comprises a core comprising said at least one pharmaceutically active agent wherein said core is made of an elastomer composition selected from the group consisting of poly(dimethylsiloxane), a siloxane-based elastomer comprising 3,3,3-trifluoropropyl groups attached to the Si-atoms of the siloxane units, a siloxane-based elastomer comprising poly(alkylene oxide) groups and mixtures thereof, and a membrane encasing said core, said membrane being made of a same or a different elastomer composition than said core, said elastomer composition being selected from the group consisting of poly(dimethylsiloxane), a siloxane-based elastomer comprising 3,3,3-trifluoropropyl groups attached to the Si-atoms of the siloxane units, a siloxane-based elastomer comprising poly(alkylene oxide) groups and mixtures thereof, and it is characterized in that the pharmaceutically active agent is selected from the group comprising anti-allergic agents, anti-inflammatory agents, anti-fungicides, glucocorticoids and mixtures thereof.

Thus, the invention concerns a delivery device consisting essentially of an elastomer composition and at least one active agent. In this application, the term "elastomer composition" may stand for one single elastomer, for a mixture of at least two elastomers that are interlaced one inside the other or in any other form of mixture, and said term may also stand for a composition comprising other components than elastomers, such as fillers. One difference with respect to the device disclosed in WO 00/33775 is that the release rate in the present invention is controlled by the properties of the core and optionally by the properties of the membrane.

According to an embodiment of the invention, said device further comprises a membrane encasing said core, made from the same or different elastomer composition, said elastomer composition being one of those listed above.

A delivery device according to the invention thus enables a constant release of one or more pharmaceutically active agents in a manner that does not cause any or minimal discomfort to the patient, and not having the above-mentioned drawbacks.

It has to be noted that the physiological conditions in an ear and a nose are different from the conditions in a uterus, for example. Indeed, in an ear for example, there are no body fluids, but a vacuum. The air is the only media moving in an ear. A person skilled in the art would therefore not readily be able to tell that the elastomer compositions listed above, that are known per se, would be suitable for otorhinological applications.

The core and the optional membrane of the device according to the invention are thus essentially made of a same or different elastomer composition that is described further below.

The elastomer composition used in the membrane, as described below, is such that it allows the predetermined, constant release rate(s) of the active agent(s). The first object of the invention is thus obtained by the choice of the elastomer composition. Secondly, the core consists essentially of an elastomer composition, that is, the core is an elastomer matrix wherein the active agents are dispersed. Therefore, even if the membrane encasing the core would be damaged, the active agents would not be released in a completely uncontrolled manner.

The release rates of the active agents can be controlled by the membrane alone or by the membrane together with the core. It is also possible that the release rate is mainly controlled by the core and that the membrane performs only the final control of the release rate. The lifetime of a device according to the invention may de customized with respect to the disease or disorder to be treated. It may typically be from 3 to 6 months, for example.

The manufacturing of delivery devices according to the invention is discussed below, even though it is well known in the art. The shape and size of the device may be quite freely chosen by the person skilled in the art, with regard to the cavity wherein the device it to be placed. It is also evident that the devices according to the invention may be applied to humans as well as to animals.

The parts of the device according to the invention may also be used in any number and in any form, as will be discussed below in the form of various embodiments of the invention.

The device according to the present invention may comprise also more than one therapeutically active agent. According to an embodiment of the invention, the core consists of one part comprising said at least one therapeutically active agent. According to another embodiment of the invention, the core consists of at least two parts each part comprising at least one therapeutically active agent. The elastomer compositions of said parts are chosen according to the release rates desired and can be the same or different in each part. According to the embodiment in which the core consists of two or more parts, the parts may be either positioned next to each other or in such a way that one part of a core encases at least partly another part of the core. Any combination of structure is naturally possible and within the scope of the invention.

According to a further embodiment of the invention, the membrane consists of at least two layers, each layer having a certain thickness. The thickness of the layers may be the same or different and the elastomer compositions used in each layer may also be the same or different. The membranes encasing each above-mentioned part of the core may also be identical or different in either the elastomer composition or the structure of the membrane (one or several layers). The combination of different layers of membrane either in thickness or in material or both, gives a further possibility for controlling the release rates of the active agents.

According to an embodiment, the device according to the invention further comprises a space separating at least two of the said at least two parts of the core and/or at least one separation membrane separating at least two of the said at least two parts of the core, said separation membrane consisting essentially of an elastomer composition. It is for example possible to produce a device according to the invention having a core consisting of three parts A, B and C, the parts A and B being separated by a space and the parts B and C being separated by a membrane. A device wherein the parts A and B are next to each other without a space or a membrane between them and the parts B and C are separated by a membrane, or a device wherein the parts A and B are separated by a membrane consisting of a first elastomer composition and the parts B and C are separated by a membrane consisting of a second elastomer composition different from the first elastomer composition, is also within the scope of this invention, as well as any other combination.

According to a further embodiment of the invention, the separation membranes are permeable or impermeable to at least one of the therapeutically active agents. It is of course possible to use a membrane that is permeable to a first active agent but impermeable to a second active agent.

According to the invention, the elastomer compositions mentioned above, namely the elastomer compositions of the core, the membrane and the possible separation membrane, are the same or different and selected from the group consisting of an elastomer composition comprising poly(dimethylsiloxane), an elastomer composition comprising a siloxane-based elastomer comprising 3,3,3-trifluoropropyl groups attached to the Si-atoms of the siloxane units, an elastomer composition comprising poly(alkylene oxide) groups, and a combination of at least two thereof.

According to an embodiment of the invention, 1 to 49.85% of the substituents attached to the Si-atoms of the siloxane units of the elastomer composition comprising a siloxane-based elastomer comprising 3,3,3-trifluoropropyl groups attached to the Si-atoms of the siloxane units are 3,3,3-trifluoropropyl groups.

According to another embodiment of the invention, said poly(alkylene oxide) groups of the elastomer composition comprising poly(alkylene oxide) groups are present as alkoxy-terminated grafts or blocks linked to the polysiloxane units by silicon-carbon bonds or as a mixture of these forms. According to yet another embodiment of the invention, the poly(alkylene oxide) groups are poly(ethylene oxide) groups.

The above-mentioned elastomer compositions are discussed below in further detail. It is also evident that other elastomer compositions than those disclosed above may additionally be used in the device according to the invention, such as biodegradable elastomers.

According to yet another embodiment of the invention, in the case there is more than one therapeutically active agent, the release rates of the at least two therapeutically active agents are identical or different. The device may also include any other therapeutically active substance that is suitably associated with a given active agent.

A person skilled in the art is readily able to determine the desired release rates of the therapeutically active agents. Examples of how to choose the elastomer composition in function of the therapeutically active agent are given in for example the Applicant's own previous patents and patent applications, as listed in the description and herein incorporated by reference.

Any combination of the embodiments mentioned above is possible and within the scope of this invention, and a person skilled in the art will be able to find the most suitable combination for a particular use.

The preparation of the device according to the invention is obvious to a person skilled in the art. Indeed, the device may be manufactured by extrusion or molding, for example. The device may also have any desired form and size. It may for example be shaped so as to fit into the existing indents of the nose or ear, or it may be shaped as a hook or rod with an enlargement at one end. As an example, it may be said that a nasal delivery device is typically 1 to 3 cm long and has a diameter of 0.5 to 5 mm. The shape and size of the device is evident for a person skilled in the art once he/she has decided the final position of the device.

The Elastomer Compositions

One of the elastomers suitable for use in the device according to this invention, particularly for use in the membrane of the device, is a siloxane-based elastomer comprising 3,3,3-trifluoropropyl groups attached to the Si-atoms of the siloxane units.

The term "siloxane-based elastomer" shall be understood to cover elastomers made of poly(disubstituted siloxanes) where the substituents mainly are lower alkyl, preferably alkyl groups of 1 to 6 carbon atoms, or phenyl groups, wherein said alkyl or phenyl can be substituted or unsubstituted. A widely used and preferred polymer of this kind is poly(dimethylsiloxane) (PDMS).

According to the invention, a certain amount of the substituents attached to the Si-atoms of the siloxane units in the elastomer shall be 3,3,3-trifluoropropyl groups. Such an elastomer can be achieved in different ways. According to one embodiment, the elastomer can be based on one single crosslinked siloxane-based polymer, such as a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) the structure of which is shown as Compound I below.

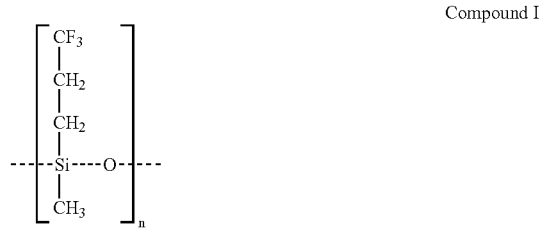

Compound I

A polymer of this kind, in which approximately 50% of the methyl substituents at the Si-atoms are replaced by 3,3,3-trifluoropropyl groups, is commercially available. The term "approximately 50%" means that the degree of 3,3,3-trifluoropropyl substitution is in fact somewhat below 50%, because the polymer must contain a certain amount (about 0.15% of the substituents) of cross-linkable groups such as vinyl or vinyl-terminated groups. Similar polymers having lower substitution degree of 3,3,3-trifluoropropyl groups can easily be synthesized.

The retarding effect of the 3,3,3-trifluoropropyl groups on the permeation of active agents across a membrane of the elastomer is dependent on the amount of these groups. Furthermore, the effect is highly dependent on the active agent used. If the elastomer is made of one single polymer only, it is necessary to prepare and use polymers with different amounts of 3,3,3-trifluoropropyl groups for different active agents.

According to another embodiment, which is particularly preferred if suitable elastomers for several different active agents are needed, is to crosslink a mixture comprising a) a non-fluorosubstituted siloxane-based polymer and b) a fluorosubstituted siloxane-based polymer, where said polymer comprises 3,3,3-trifluoropropyl groups attached to the Si-atoms of the siloxane units. The first ingredient of the mixture, the non-fluorosubstituted polymer, can be any poly(disubstituted siloxane) where the substituents mainly are lower alkyl, preferably alkyl groups of 1 to 6 carbon atoms, or phenyl groups, wherein said alkyl or phenyl can be substituted or unsubstituted. The substituents are most preferably alkyl groups of 1 to 6 carbon atoms. A preferred non-fluorosubstituted polymer is PDMS. The second ingredient of the mixture, the fluorosubstituted polymer, can for example be a poly(dialkyl siloxane) where a certain amount of the alkyl groups at the Si-atoms are replaced by 3,3,3-trifluoropropyl groups. A preferred example of such polymers is poly(3,3,3-trifluoropropyl methyl siloxane) as mentioned above. A particularly preferable polymer of this kind is a polymer having as high amount of 3,3,3-trifluoropropyl substituents as possible, such as the commercially available polymer, in which approximately 50% of the methyl substituents at the Si-atoms are replaced by 3,3,3-trifluoropropyl groups. An elastomer with great permeation retarding effect can be achieved by using exclusively or mainly the aforementioned polymer. Elastomers with less retarding influence on the permeation of the active agent can be obtained by using mixtures with increasing amounts of the non-fluorosubstituted siloxane-based polymer.

Another elastomer that can be used in this invention comprises poly(alkylene oxide) groups so that the poly (alkylene oxide) groups are present in the said elastomer either as alkoxy-terminated grafts of polysiloxane units or as blocks, the said grafts or blocks being linked to the polysiloxane units by silicon-carbon bonds. The poly(alkylene oxides) may also be present as a blend of the options mentioned. The second elastomer may be a siloxane-based elastomer, suitably a poly(dimethyl siloxane)-based elastomer. The said second elastomer may possibly also comprise poly(alkylene oxide) groups. These poly(alkylene oxide) groups may also be present either as alkoxy-terminated grafts of poly(dimethyl siloxane) units or as blocks, the said grafts or blocks being linked to the poly(dimethyl siloxane) units by silicon-carbon bonds. The poly(alkylene oxides) may also in this elastomer be present as a blend of the options mentioned above.

According to an embodiment of the invention, the elastomer composition may be a blend which comprises a siloxane-based elastomer, which is, for example, made up of PDMS, and at least one straight-chain polysiloxane copolymer which comprises poly(alkylene oxide) groups. In this case the poly(alkylene oxide) groups are present in the said polymer either as alkoxy-terminated grafts of polysiloxane units or as blocks, the said grafts or blocks being linked to the polysiloxane units by silicon-carbon bonds. The poly (alkylene oxide) groups may, of course, also be present in the polymer as a blend of the forms mentioned. In this embodiment, also the siloxane-based elastomer may comprise poly(alkylene oxide) groups, in which case these poly(alkylene oxide) groups are present in the elastomer either as alkoxy-terminated grafts of polysiloxane units or as blocks, the said blocks or grafts being linked to the polysiloxane units by silicon-carbon bonds. The poly(alkylene oxide) groups may also be present as a blend of the forms mentioned.

Of course, the elastomer composition may also be made up of two elastomers interlaced one inside the other, as above, and at least one straight-chain polysiloxane copolymer which comprises poly(alkylene oxide) groups.

The poly(alkylene oxide) groups of the elastomer composition may suitably be, for example, poly(ethylene oxide) groups (PEO groups).

The polysiloxane units of the elastomer composition are preferably groups having the formula

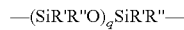

where R' and R" are
partly free groups, which are the same or different and which are a lower alkyl group, or a phenyl group, in which case the said alkyl or phenyl groups may be substituted or unsubstituted, or alkoxy-terminated poly (alkylene oxide) groups having the formula

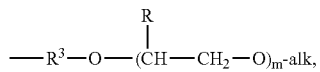

where alk is a lower alkyl group, suitably methyl, R is hydrogen or a lower alkyl, m is 1 . . . 30, and $R^3$ is a straight or branched $C_2$-$C_6$ alkyl group,
partly bonds, formed from the hydrogen or alkylene groups, to other polymer chains in the elastomer, and possibly partly unreacted groups, such as hydrogen, vinyl or vinyl-terminated alkene, and q is 1 . . . 3000.

The term "lower alkyl" stands here and generally in the description of the present invention for $C_1$-$C_6$ alkyl groups.

The above-mentioned free R' and R" groups are suitably a lower alkyl group, preferably methyl.

The term "poly(alkylene oxide) group" means that said group comprises at least two alkyl ether groups successively connected to each other.

According to a preferred embodiment, the poly(alkylene oxide) groups are present in the elastomer in the form of poly(alkylene oxide) blocks having the formula

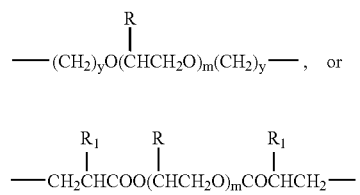

where R is hydrogen, a lower alkyl or a phenyl,
$R_1$ is hydrogen or a lower alkyl, y is 2 . . . 6, and m is 1 . . . 30.

Preferable combinations of elastomers are PDMS with poly(ethylene oxide)-PDMS for the nasal delivery devices and PDMS with fluorosubstituted PDMS for the otological delivery devices.

The elastomer composition preferably comprises a filler, such as amorphous silica, in order to give a sufficient strength for the membrane made from said elastomer. It is also possible to include other additives, while taking into account that they need to be biocompatible and harmless to the subject.

The Pharmaceutically Active Agents

Different active agents may be used in the delivery device according to the invention. Suitable active agents for incorporation into a device of the present invention include those that provide the desired release profile and therapeutic effect, and that exhibit an acceptably low level of ototoxicity and/or nasal toxicity. Some of the conditions that may be treated with an active agent delivered from a delivery device according to the invention are nasal inflammatory disorders, allergic reactions, asthma and fungal infections as well as otitis, acute infections, cochlear and vestibular disorders, vertigo and Meniere's disease, sudden deafness, sensoneurinal hearing loss, tinnitus and motion sickness. Further conditions to be treated include endolymphatic hydrops, endolymphatic hypertension, perilymphatic hypertension, perilymphatic hydrops, perilymphatic fistula, intracochlear fistula and ruptures in various membrane structures within the ear.

Generic examples of pharmaceutically active agents include antimicrobial agents such as antibacterial agents, anti-infective agents including antibiotics, antifungals and antivirals, antihistamines, antivertigo drugs (for example for the treatment of Meniere's disease, sympathomimetics, corticosteroids, vasodilators (for the treatment of sudden hearing loss), genes, vectors, chemotherapeutic agents and adenovirus-type agents.

Specific examples of pharmaceutically active agents include: Acedapsone, Acediasulfone, Aconiazide, Acrosoxacin, Amifloxacin, Amikacin, Aminosalicylates, Aminosalicylic Acid, Benzamidosalicylate, Phenyl Aminosalicylate, Amoxycillin, Amoxycillin Trihydrate, Amphomycin, Ampicillin, Ampicillin Trihydrate, Apalcillin, Apramycin, Arbekacin, Arsanilic Acid, Aspoxicillin, Astromicin, Avoparcin, Azidamfenicol, Azidocillin, Azithromycin, Azlocillin, Aztreonam, Bacampicillin Bacitracin, Balofloxacin, Bambermycin, Bekanamycin, Benethamine Penicillin, Benzathine Penicillin, Benzathine Phenoxymethylpenicillin, Benzylpenicillin, Biapenem, Brodimoprim, Calcium Sulphaloxate, Capreomycin, Carbadox, Carbenicillin, Carfecillin, Carindacillin, Carumonam, Cefaclor, Cefadroxil, Cefapirin, Cefatrizine, Cefazedone, Cefbuperazone, Cefcanel Daloxate, Cefdinir, Cefditoren, Cefepime, Cefetamet, Cefixime, Cefmenoxime, Cefmetazole, Cefminox, Cefodizime, Cefonicid, Cefoperazone, Ceforanide, Cefotaxime, Cefotetan, Cefotiam, Cefoxitin, Cefozopran, Cefpimizole, Cefpiramide, Cefpiramide, Cefpirome, Cefpodoxime Proxetil, Cefprozil, Cefroxadine, Cefsulodin, Ceftazidime, Cefteram, Ceftezole, Ceftibuten, Ceftiofur, Ceftizoxime, Ceftriaxone, Cefuroxime, Cefuroxime Axetil, Cefuroxime, Cefuzonam, Cephacetrile, Cephalexin, Cephalexin, Cephalonium, Cephaloridine, Cephalothin, Cephamandole, Cephamandole Nafate, Cephamandole, Cephazolin, Cephazolin, Cephradine, Chloramphenicol, Chloramphenicol Palmitate, Chloramphenicol Succinate, Chlorquinaldol, Chlortetracycline, Ciclacillin, Cilastatin, Cinoxacin, Ciprofloxacin, Ciprofloxacin Lactate, Clarithromycin, Clavulanic Acid, Clemizole Penicillin, Clinafloxacin, Clindamycin, Clindamycin Palmitate, Clioquinol, Clofazimine, Clofoctol, Cloxacillin, Cloxacillin Benzathine, Cloxacillin, Colistin, Colistin Sulphomethate, Co-tetroxazine, Co-trifamole, Co-trimazine, Co-trimoxazole, Cranberry, Cyacetazide, Cycloserine, Dapsone, Daptomycin, Demeclocycline, Demeclocycline, Dibekacin, Dicloxacillin, Difloxacin, Dihydrostreptomycin, Dirithromycin, Doxycycline, Doxycycline Fosfatex, Enoxacin, Enramycin, Enrofloxacin, Epicillin, Erythromycin, Erythromycin Acistrate, Erythromycin Estolate, Erythromycin Ethyl Succinate, Erythromycin Gluceptate, Erythromycin Lactobionate, Erythromycin Propionate, Erythromycin Stearate, Ethambutol, Ethionamide, Fibracillin, Fleroxacin, Flomoxef, Flucloxacillin, Flucloxacillin, Flucloxacillin, Flumequine, Flurithromycin, Formosulphathiazole, Fosfomycin, Fosmidomycin, Framycetin, Furaltadone, Fusalfungine, Fusidic Acid, Diethanolamine Fusidate, Gentamicin, Gramicidin, Grepafloxacin, Halquinol, Hetacillin, Hetacillin, Hexamine, Hexamine Hippurate, Hexamine Mandelate, Hydrabamine Phenoxymethylpenicillin, Imipenem, Icepamicin, Isoniazid, Josamycin, Josamycin Propionate, Kanamycin, Kitasamycin, Latamoxef, Lenampicillin, Levofloxacin, Lincomycin, Lomefloxacin, Loracarbef, Lymecycline, Mafenide Acetate, Magainins, Mandelic Acid, Mecillinam, Meclocycline Sulfosalicylate, Meropenem, Metampicillin, Methacycline, Methaniazide, Methicillin, Methocidin, Metioprim, Mezlocillin, Micronomicin, Midecamycin, Minocycline, Miocamycin, Mocimycin, Morinamide, Methaniazide, Methicillin, Methocidin, Metioprim, Mezlocillin, Micronomicin, Midecamycin, Minocycline, Miocamycin, Mocimycin, Morinamide, Mupirocin, Nadifloxacin, Nafcillin, Nalidixic Acid, Neomycin, Neomycin Undecenoate, Netilmicin, Nifuroxazide, Nifurtoinol, Nifurzicle, Nisin, Nitrofurantoin, Nitrofurazone, Nitroxoline, Norfloxacin, Nosiheptide, Novobiocin, Ofloxacin, Oleandomycin, Oxacillin, Oxolinic Acid, Oxytetracycline, Panipenem, Paromomycin, Pefloxacin Mesylate, Penimepicycline, Phenethicillin, Phenoxymethylpenicillin, Phenoxymethylpenicillin Calcium, Phenoxymethylpenicillin Potassium, Phthalylsulphathiazole, Pipemidic Acid, Piperacillin, Piromidic Acid, Pivampicillin, Pivampicillin, Pivcephalexin, Pivmecillinam, Pristinamycin, Polymyxin B, Procaine Penicillin, Propicillin, Prothionamide, Pyrazinamide, Ramoplanin, Ribostamycin, Rifabutin, Rifampicin, Rifamycin, Rifapentine, Rifaximin, Rokitamycin, Rolitetracycline, Rosaramicin, Roxithromycin, Rufloxacin, Sulphadiazine, Sissomicin, Sparfloxacin, Spectinomycin, Spiramycin, Stearylsulfamide, Streptomycin, Succinyisulphathiazole, Sulbactam, Sulbenicillin Sodium, Sulfabenzamide, Sulfacytine, Sulfadicramide, Sulfadoxine, Sulfamerazine, Sulfamethylthiazole, Sulfametopyrazine, Sulfametrole, Sulfaperin, Sulfaquinoxaline, Sulfasuccinamide, Sulfenazone, Sulphacetamide, Sulphadiazine, Sulphadimethoxine, Sulphadimidine, Sulphafurazole, Acetyl Sulphafurazole, Sulphafurazole Diethanolamine, Sulphaguanidine, Sulphaguanole, Sulphamethizole, Sulphamethoxazole, Sulphamethoxypyridazine, Acetyl Sulphamethoxypyridazine, Sulphamoxole, Sulphanilamide, Sulphapyridine, Sulphasomidine, Sulphathiazole, Sulphathiazole, Sulphatolamide, Sulphaurea, Sultamicillin, Talampicillin, Talampicillin Napsylate, Taurolidine, Tazobactam, Teicoplanin, Temafloxacin, Temocillin, Terizidone, Tetracycline, Tetracycline Phosphate Complex, Tetroxoprim, Thenoic Acid, Thiacetazone, Thiamphenicol, Thiamphenicol Glycinate, Thiocarlide, Thiostrepton, Ticarcillin, Tigemonam, Tobramycin, Tobramycin, Tosufloxacin, Triacetyloleandomycin, Trimethoprim, Trospectomycin, Trovafloxacin, Tylosin, Tylosin Tartrate, Tyrothricin, Vancomycin, Viomycin, Virginiamycin and Xibornol as antibacterial agents; Adrenaline, Adrenaline Acid Tartrate, Adrenalone, Amezinium Methylsulphate, Angiotensin Amide, Arbutamine, Bambuterol, Bitolterol Mesylate, Broxaterol, Buphenine, Carbuterol, Clenbuterol, Clonazoline, Clorprenaline, Denopamine, Dimepropion, Dimetofrine, Dipivefrine, Dobutamine, Docarpamine, Dopamine, Dopexamine, Eformoterol Fumarate, Ephedra, Ephedrine, Etafedrine, Ethylnoradrenaline, Etifelmine, Etilefrine, Fenoterol, Fenoxazoline, Gepefrine Tartrate, Hexoprenaline, Hexoprenaline, Hydroxyamphetamine, Ibopamine, Indanazoline, lsoetharine, Isoetharine Mesylate, lsometheptene, lsometheptene Mucate, Isoprenaline, Isoxsuprine, Levonordefrin, Mabuterol, Mephentermine, Mephentermine, Metaraminol Tartrate, Methoxamine, Methoxyphenamine, Methylephedrine, Midodrine, Naphazoline, Noradrenaline, Noradrenaline Acid Tartrate, Norfenefrine, Octodrine, Octopamine, Orciprenaline, Oxedrine, Oxedrine Tartrate, Oxilofrine, Oxilofrine, Oxymetazoline, Phenylephrine, Phenylephrine Acid Tartrate, Phenylpropanolamine, Pholedrine, Pirbuterol Acetate, Prednazoline, Prenalterol, Procaterol, Protokylol, Pseudoephedrine, Reproterol, Rimiterol, Ritodrine, Salbutamol, Salmeterol Xinafoate, Terbutaline, Tetrahydrozoline, Tramazoline, Tretoquinol, Tuaminoheptane, Tulobuterol, Tymazoline, Xamoterol, Xamoterol Fumarate and Xylometazoline as sympathomimetics; Acrivastine, Antazoline, Antazoline Mesylate, Astemizole, Azatadine Maleate, Azelastine, Bamipine, Bromodipbenhydramine, Brompheniramine Maleate, Dexbrompheniramine Maleate, Buclizine, Carbinoxamine Maleate, Cetirizine, Chlorcyclizine, Chloropyrilene Citrate, Chlorpheniramine Maleate, Dexchlorpheniramine Maleate, Chlorphenoxamine, Cinnarizine, Clemastine Fumarate, Clemizole, Clocinizine, Cyclizine, Cyclizine Lactate, Cyclizine Tartrate, Cyproheptadine, Deptropine Citrate, Dimenhydrinate, Dimethindene Maleate, Dimethothiazine Mesylate, Diphenhydramine, Diphenhydramine Citrate, Diphenhydramine Di(acefyllinate), Diphenylpyraline Hydrochloride, Doxylamine Succinate, Ebastine, Embramine, Emedastine, Epinastine, Flunarizine, Halopyramine, Histapyrrodine, Histapyrrodine, Homochlorcyclizine, Hydroxyethylpromethazine Chloride, Hydroxyzine Embonate, Hydroxyzine, Isothipendyl, Levocabastine, Loratadine, Mebhydrolin, Mebhydrolin Napadisylate, Meclozine, Mefenidramium Methylsulphate, Mepyramine, Mepyramine Maleate, Mequitazine, Methapyrilene Fumarate, Methapyrilene, Methdilazine, Mizolastine, Niaprazine, Noberastine, Oxatomide, Oxomemazine, Phenindamine Tartrate, Pheniramine, Pheniramine Aminosalicylate, Pheniramine Maleate, Phenyltoloxamine Citrate, Pimethixene, Piprinhydrinate, Promethazine, Promethazine Theoclate, Propiomazine, Propiomazine Maleate, Setastine, Tazifylline, Terfenadine, Thenalidine Tartrate, Thenyldiamine, Thiazinamium Methylsulphate, Thiethylperazine, Thiethylperazine Malate, Thiethylperazine Maleate, Thonzylamine, Tolpropamine, Trimeprazine Tartrate, Trimethobenzamide, Tripelennamine Citrate, Tripelennamine, Triprolidine and Tritoqualine as antihistamines.

Muscarinic and/or opioid agents may be used for the treatment of tinnitus, for example an anticholinesterase inhibitor, such as neostigmine. The opioid agent may be an agonist. Other possible agents are morphine, DAMGO, heroin, hydromorphone, dermorphin, spiradoline, U50,488, dynorphin A, DPDPE, deltorphin, DSLET, oxymorphone, levorphanol, methadone, meperidine, fentanyl, codeine, hydrocodone, oxycodone, propoxyphene, tramadol, etorphine, EKC, meperidine or their pharmaceutically acceptable salts, prodrugs and derivatives. Preferred opioid receptor agonist-antagonists include, but are not limited to, buprenorphine, butorphanol pentazocine and nalbuphine. A botulinum toxin may also be used as well as benzodiazepine tranquilizers such as valium and alprazolam. Also a local anesthetic such as lidocaine, tetracaine, prilocaine, bupivacaine, mepivacaine, procaine and/or benzocaine may be used. It has equally been reported that loop diuretics may be used for the treatment of tinnitus, such as furosemide, ethacrynic acid and bumetanide.

Said botulinum toxin may also be used to alleviate cochlear nerve dysfunction and Meniere's disease. Pharmaceutically active agents useful for example for nerve cell damage in cochlear disease may also be used in the device according to the invention, as well as antivirals and osmotic agents such as salts or glycerine.

Infections of the ear such as otitis may be treated with amoxicillin, ampicillin, a mixture of ciprofloxacin and hydrocortisone. Anti-infective agents such as iodine, aminoglycosides, penicillins, cephalosporins, polymyxin, ofloxacillins, gentamycin, cephazolin, clindamycin, tetracyclines and their analogs are commonly used also, as well as anti-inflammatory agents such as steroids and non-steroidal anti-inflammatories. Non-steroidal anti-inflammatories include compounds such as propionic acid derivatives such as benoxaprofen, carprofen, flurbiprofen, fenoprofen, fenbufen, ibuprofen, indoprofen, ketoprofen, naproxen, miroprofen, oxaprozin, pranoprofen, pirprofen, suprofen, tiaprofenic acid, fluprofen, alminoprofen, bucloxic acid and the like; acetic acid derivatives such as alclofenac, acematacin, aspirin, diclofenac, indomethacin, ibufenac, isoxepac, furofenac, fentiazac, clidanac, oxpinac, sulindac, tolmetin, zomepirac, zidometracin, tenclofenac, tiopinac, and the like; fenamic acid derivatives such as mefenamic acid, flufenamic acid, niflumic acid, meclofenamic acid, tolfenamic acid, and the like; biphenylcarboxylic acid derivatives such as diflunisol, flufenisol, and the like; oxicam derivatives such as isoxicam, piroxicam, sudoxicam, and the like; cyclosporin, indomethacin, and naproxen. Other drugs include potassium chloride, potassium carbonate, and the like. Anti-prostaglandins may also be used.

Some spesific examples of corticosteroids include Alclometasone Dipropionate, Aldosterone, Amcinonide, Beclomethasone Dipropionate, Bendacort, Betamethasone, Betamethasone Acetate, Betamethasone Benzoate, Betamethasone Dipropionate, Betamethasone Valerate, Budesonide, Ciclomethasone, Ciprocinonide, Clobetasol Propionate, Clobetasone Butyrate, Clocortolone Pivalate, Cloprednol, Cortisone Acetate, Cortivazol, Deflazacort, Deoxycortone Acetate, Deoxycortone Pivalate, Deprodone, Desonide, Desoxymethasone, Dexamethasone, Dexamethasone Acetate, Dexamethasone Isonicotinate, Dichlorisone Acetate, Diflorasone Diacetate, Diflucortolone Valerate, Difluprednate, Domoprednate, Endrysone, Fluazacort, Fluclorolone Acetonide, Fludrocortisone Acetate, Flumethasone, Flumethasone Pivalate, Flunisolide, Fluocinolone, Fluocinolone Acetonide, Fluocinonide, Fluocortin Butyl, Fluocortolone, Fluocortolone Hexanoate, Fluocortolone Pivalate, Fluorometholone, Fluorometholone Acetate, Fluprednidene Acetate, Fluprednisolone, Flurandrenolone, Fluticasone Propionate, Formocortal, Halcinonide, Halobetasol Propionate, Halometasone, Hydrocortamate Hydrochloride, Hydrocortisone, Hydrocortisone Acetate, Hydrocortisone Butyrate, Hydrocortisone Cypionate, Hydrocortisone Hemisuccinate, Hydrocortisone Sodium Phosphate, Hydrocortisone Sodium Succinate, Hydrocortisone Valerate, Medrysone, Meprednisone, Methylprednisolone, Methylprednisolone Acetate, Methylprednisolone Hemisuccinate, Methylprednisolone Sodium Succinate, Mometasone Furoate, Paramethasone Acetate, Prednicarbate, Prednisolamate Hydrochloride, Prednisolone, Prednisolone Acetate, Prednisolone Hemisuccinate, Prednisolone Hexanoate, Prednisolone Pivalate, Precinisolone Sodium Metasulphobenzoate, Prednisolone Sodium Phosphate, Prednisolone Sodium Succinate, Prednisolone Steaglate, Prednisolone Tebutate, Prednisone, Prednisone Acetate, Prednylidene, Procinonide, Rimexolone, Suprarenal Cortex, Tixocortol Pivalate, Triamcinolone, Triamcinolone Acetonide, Triamcinolone Diacetate and Triamcinolone Hexacetonide.

It is also known to use antifungal agents and antiviral agents in the treatment of the various diseases listed above. Antifungal drugs are incorporated into the polymer for the treatment of fungal sinusitis, and anti-inflammatory and anti-infective drugs are incorporated for the treatment of chronic bacterial sinusitis, for example. Examples of antifungal agents include nystatin, griseofulvin, lotrimin, mycostatin, ketoconazole, amphotericin B and analogs thereof and examples of antiviral agents include idoxuridine, amantadine, vidarabine, interferon, acyclovir, and analogues thereof.

The devices according to the invention may further contain fluorides or other medicaments for the treatment of otosclerosis.

Other pharmaceutically active agents that may be used in the otological delivery device according to the invention include urea, mannitol, sorbitol, glycerol, lidocaine, xylocaine, epinephrine, immunoglobulins, sodium chloride, steroids, heparin, hyaluronidase, aminoglycoside antibiotics (streptomycin/gentamycin), antioxidants, neurotrophins, nerve growth factors, various therapeutic peptides and polysaccharides.

It has also been described that calcium channel blockers, free radical scavengers, corticosteroids, antagonists of glutamate-N-methyl-D-aspartate (NMDA) and non-NMDA receptors and various thrombolytic agents may be used in the treatment of hearing loss, tinnitus and vertigo.

For nasal devices, anti-asthmatic drugs such as of the β2-adrenoceptor agonist, antimuscarines, cromoglycates, leucotrienes, xanthine or corticosteroid type may be used, among others.

As is evident from the lists above, any pharmaceutically active agent that has an acceptably low level of toxicity at the position of the delivery device may be used in a device according to this invention. The above list is thus not to be construed as limiting the scope of protection of the present claims. A person skilled in the art is naturally able to determine the amount of active agent(s) and the nature of it (them) as well as the nature of any mixture of active agents to be used for a particular purpose.

Suitable indications for nasal devices are for example allergies, such as perennial allergic rhinitis. Suitable indications for otological devices are for example senso-neurinal hearing loss, sudden deafness, Meniere's disease and tinnitus. Suitable active agents for these indications are corticosteroids, antibiotics of the gentamycin class, growth factors and antivirals.

The Placement of the Delivery Device

The otological device may be placed in any appropriate location in the internal or middle ear. It may also be placed partly in the outer ear and partly in the middle ear. By outer ear, it is meant here the auricle and the acoustic meatus. By middle ear, it is meant the eardrum, the auditory ossicles and the Eustachian tube. The internal ear stands for the posterior and superior semicircular canals as well as for the vestibular, facial and cochlear nerves.

The delivery device is preferably introduced through the eardrum and glued to place with fibrin glue or other suitable material. In the unexpected case of detachment of the device, it would just lie in the bottom of the middle ear cavity where it would do no harm. Round window niche has specifically been found to be permeable to many substances. Therefore the device according to the present invention is advantageously shaped and sized for placement of at least a part of it in the round window niche.

The nasal device may be positioned in the nasal conchas or the Eustachian tube. It is preferably positioned in the interior nasal conchas.

The otological device is preferably positioned in the round window niche. Since the round window is roughly cylindrical, the largest releasing surface would be that of a cylinder, for both direct and collateral release.

One or more of the devices may be introduced to a patient's ear or nose (one or more per nostril, for example) and these devices may contain the same or different active agent.

The invention is described below in greater detail by the following, non-limiting drawings and examples.

DETAILED DESCRIPTION OF THE DRAWINGS

Figure 1:
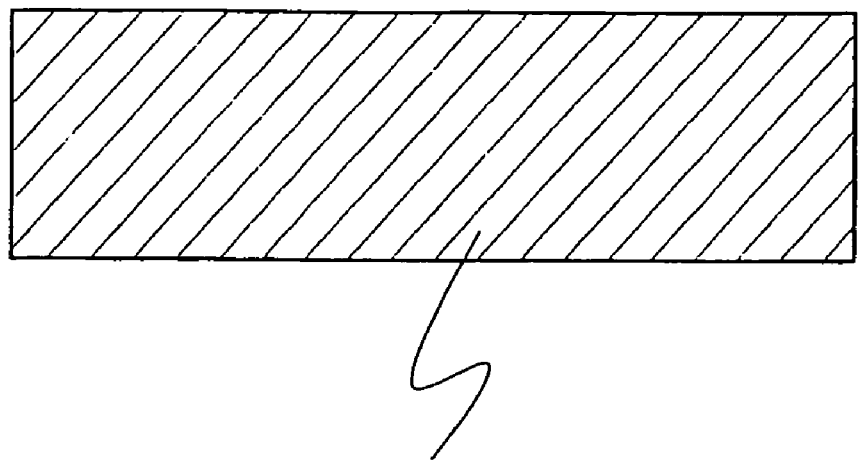
FIG. 1 illustrates a delivery device according to a first embodiment of the invention.

FIG. 1 illustrates a delivery device according to a first embodiment of the invention, said device comprising a core 1.

Figure 2:
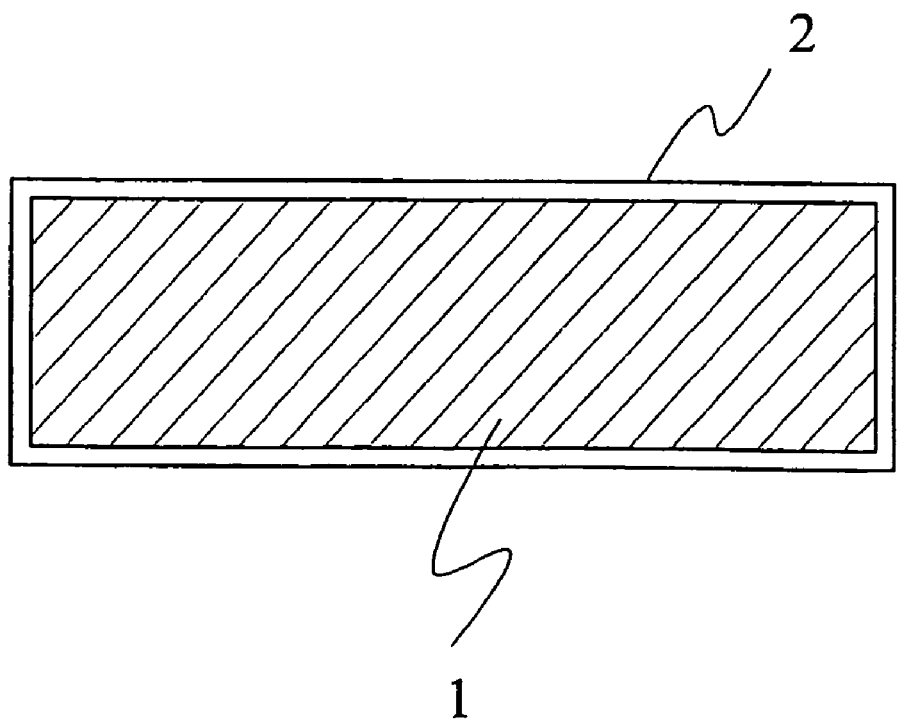
FIG. 2 illustrates a delivery device according to a second embodiment of the invention.

FIG. 2 illustrates a delivery device according to a second embodiment of the invention. The device comprises a core 1 and a membrane 2 encasing said core and situated next to it. In the Figure, however, the membrane 2 is shown somewhat apart from the core, for sake of clarity.

Figure 3:
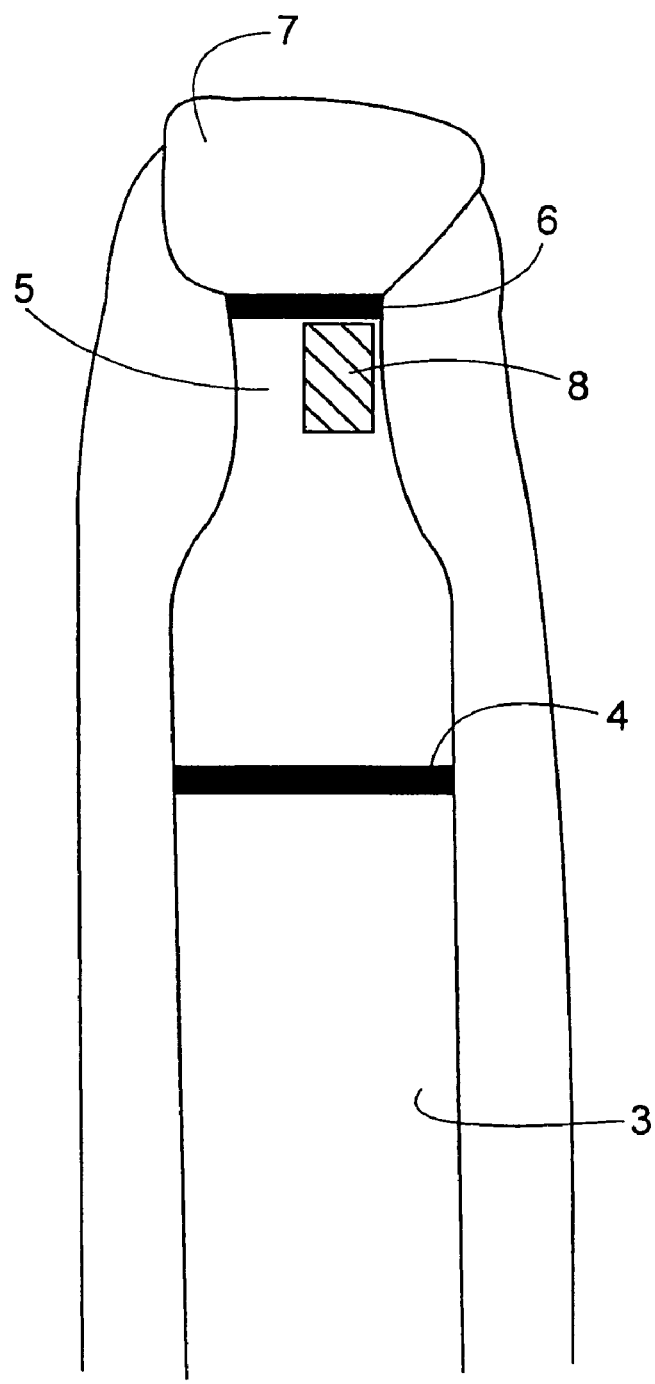
FIG. 3 illustrates a delivery device according to the invention in an ear.

FIG. 3 illustrates a delivery device according to the invention placed in a patient's ear. The ear is shown in cross-sectional view. The Figure shows the ear canal 3, the tympanic membrane 4, the round window niche 5, the round window membrane 6 and the inner ear 7. The Figure further shows a delivery device 8 positioned near the round window membrane.

Figure 4:
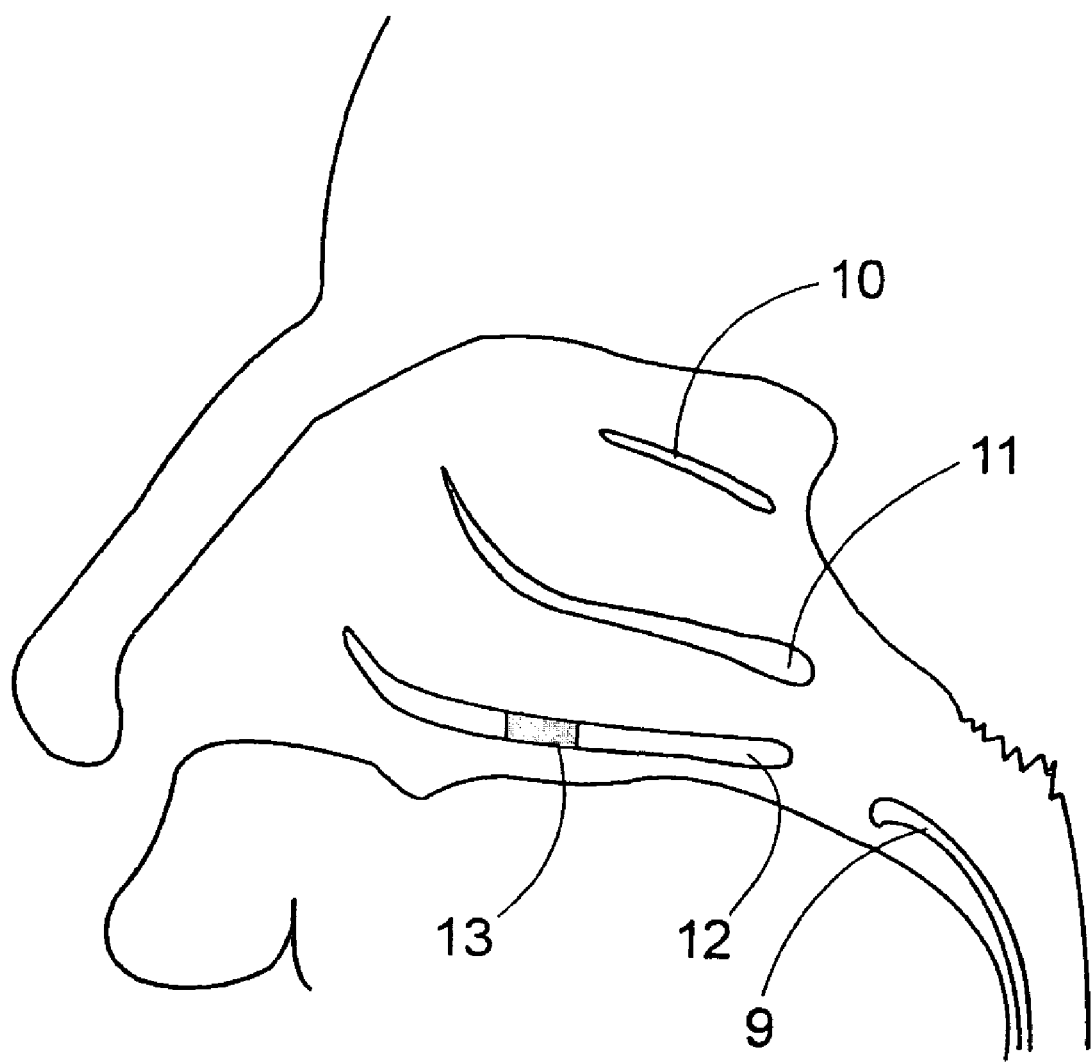
FIG. 4 illustrates a delivery device according to the invention in a nose.

FIG. 4 illustrates a delivery device according to the invention placed in a patient's nose. The nose is shown in cross-sectional view. The Figure shows the superior nasal concha 10, the middle nasal concha 11, the inferior nasal concha 12 and the Eustachian tube 9. The Figure further shows a delivery device 13 in its position of use in the inferior nasal concha 12.

Figure 5:
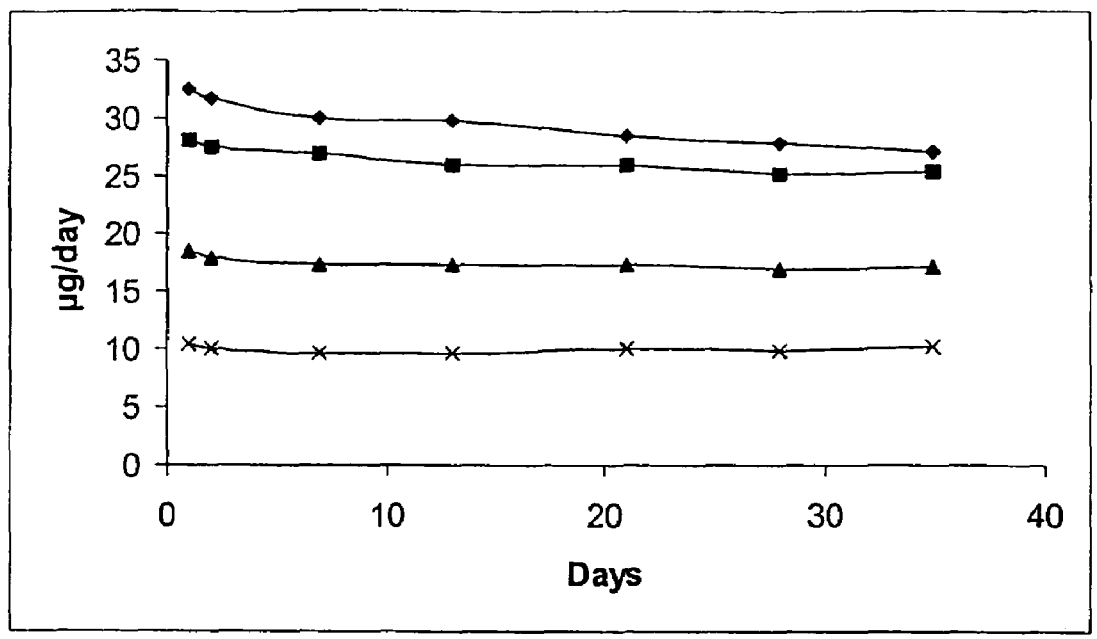
FIG. 5 illustrates the results of Example 1.
Figure 6:
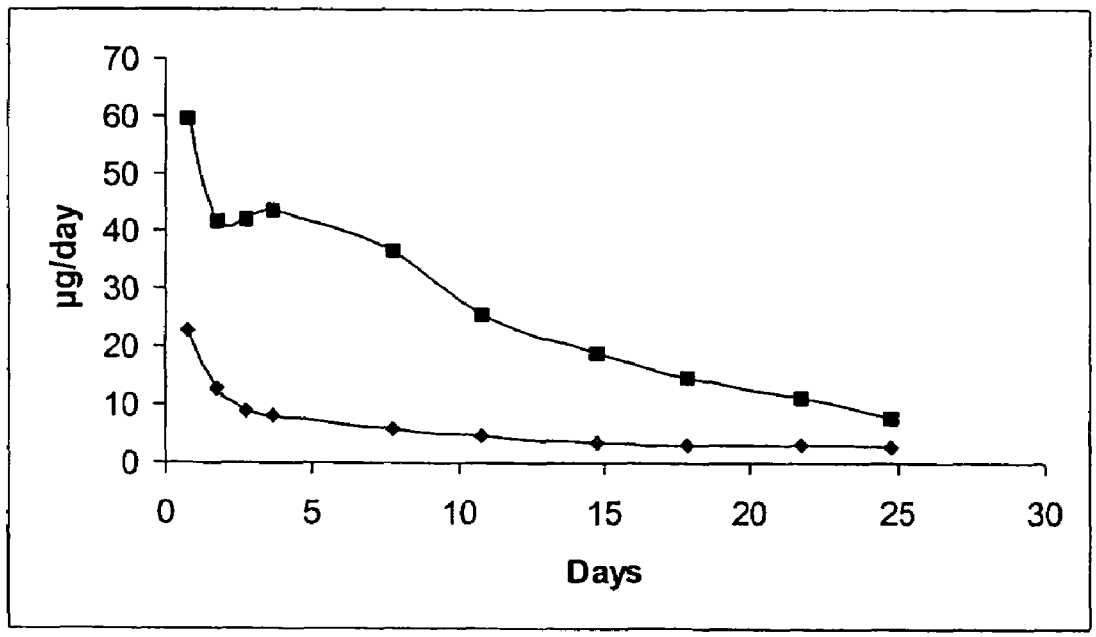
FIG. 6 illustrated the results of Examples 2 to 5.

FIGS. 5 and 6 are discussed in detail below.

In this specification, except where the context requires otherwise, the words "comprise", "comprises" and "comprising" means "include", "includes" and "including", respectively. That is, when the invention is described or defined as comprising specified features, various embodiments of the same invention may also include additional features.

EXPERIMENTAL PART

Example 1

The therapeutically active agent beclomethasone's concentrations in ng/ml or pg/μl in perilymfe of ipsilateral ear of guinea pigs treated with round window implants according to the present invention were measured.

Implants of PDMS without therapeutically active agents (placebo), PDMS with 0.5 mg beclomethasone (low dose implant), PEO-PDMS with 0.5 mg beclomethasone (high dose implant) or not treated at all (detection limit 2.25 pg/μl) were used. The preparation of the various implants is described below.

Low Dose Implant 39.4 parts of commercial poly(dimethylsiloxane-co-vinylmethylsiloxane), 0.4 parts poly(hydrogenmethylsiloxane-co-dimethylsiloxane) crosslinker, 0.02 parts ethinyl cyclohexanol inhibitor and 10 ppm Pt-catalyst (of the reaction species) in vinyl-methyl-siloxane were mixed in a two-chamber mixer. 60 parts (by weight) of drug were mixed in a two-chamber mixer. The mixture was extruded through dies to desired dimensions (diameter (OD) 1.14 mm) and crosslinked in an oven by heat. The cores were removed, cooled and cut to desired length (0.8 mm). The content of the drug was 60% (wt/wt) based on HPLC assay.

High Dose Implant 39.4 parts of commercial poly(triethyleneoxide-b-deka (dimethylsiloxane))triethyleneoxide vinyl ether terminated, 0.4 parts poly(hydrogenmethylsiloxane-co-dimethylsiloxane) crosslinker, 0.02 parts ethinyl cyclohexanol inhibitor and 10 ppm Pt-catalyst (of the reaction species) in vinyl-methyl-siloxane were mixed in a two-chamber mixer. 60 parts (by weight) of drug were mixed in a two-chamber mixer. The mixture was extruded through dies to desired dimensions (OD 1.14 mm) and crosslinked in an oven by heat. The cores were removed, cooled and cut to desired length (0.8 mm). The content of the drug was 60% (wt/wt) based on HPLC assay.

Placebo 99.4 parts of commercial poly(dimethylsiloxane-co-vinylmethylsiloxane), 0.4 parts poly-(hydrogenmethylsiloxane-co-dimethylsiloxane) crosslinker, 0.02 parts ethinyl cyclohexanol inhibitor and 10 ppm Pt-catalyst (of the reaction species) in vinyl-methyl-siloxane were mixed in a two-chamber mixer. The mixture was extruded through dies to desired dimensions (OD 1.14 mm) and crosslinked in an oven by heat. The cores were removed, cooled and cut to desired length (0.8 mm).

A device according to the present invention as described above, each device consisting of one of the above-mentioned elastomer compositions and having the mentioned amount of therapeutically active agent or no agent, was introduced into the perilymfe of ipsilateral ear of guinea pigs (25 animals in each group), into the round window of the right side ear of the animal, except for one animal in each group.

The release of the beclomethasone was measured at days 1, 14 and 28 after the treatment, i.e. positioning of the device. All PEO-PDMS implants released until day 28, while one of the five PDMS implants appeared not to do so at day 28. The concept of release of drugs from round window polymer implants into the inner ear fluid is thus proven.

In general, the concentrations of beclomethasone were higher with PEO-PDMS polymers. The results are given below in Table 1.

TABLE 1

| Treatment/Timepoint* | Day 1 | Day 14 | Day 28 |
|---|---|---|---|
| Not operated | Not done | Not done | 0 |
|  |  |  | 0 |
|  |  |  | 0 |
|  |  |  | 0 |
|  |  |  | 0 |
| PDMS implant only | 0 | 0 | 0 |
|  | 0 | 0 | 0 |
|  | 0 | 0 | 0 |
|  | 0 | 0 | 0 |
|  | 0 | 0 | 0 |
| PDMS + 0.5 mg beclomethasone ("low dose") | 75 | 61 | 3.9 |
|  | 262 | 43.8 | 0 |
|  | 16.6 | 6.4 | 21.2 |
|  | 34.9 | 101 | 172 |
|  | 30.7 | 2.9 | 4.7 |
| PEO-PDMS + 0.5 mg beclomethasone ("high dose") | 43 | 121 | 60.5 |
|  | 193 | 28.2 | 731 |
|  | 96.6 | 46.9 | 10.3 |
|  | 64.3 | 85.4 | 602 |
|  | 55.6 | 7.6 | 26.9 |

*Day after implant insertion

The animals that had not been operated were not sacrificed on days 1 and 14. On day 21, all five animals were sacrificed and there was no release of beclomethasone. There was also no release of beclomethasone in the animals that had received the placebo. The other results can be seen in the Table and are further illustrated in FIG. 5. In FIG. 5, the squares illustrate the high dose implants and the losanges the low dose implants.

Furthermore, release rates of a nasal device were studied in vitro. For the study, the following membranes and cores were prepared, followed by the implant preparation.

Example 2

30% PEO-b-PDMS Membrane Preparation 29 parts of commercial poly(triethyleneoxide-b-deka (dimethylsiloxane))triethyleneoxide vinyl ether terminated, 69 parts silica-filled poly(dimethylsiloxane-co-vinylmethylsiloxane), 10 ppm Pt-catalyst (of the reacting species) and 0.03 parts inhibitor (ethynyl cyclohexanol), approx. 2 parts of poly-(hydrogenmethylsiloxane-co-dimethylsiloxane) crosslinker were mixed with a 2-roll mill. The mixture was extruded to a tube-like form with a wall thickness of 0.3 mm and cured by heat.

Core Preparation 19.7 parts of commercial poly(triethyleneoxide-b-deka (dimethylsiloxane))triethyleneoxide vinyl ether terminated, 19.7 parts poly(dimethylsiloxane-co-vinylmethylsiloxane) and 10 ppm Pt-catalyst (of the reacting species) and 0.02 parts inhibitor (ethynyl cyclohexanol), approx. 0.6 parts of poly(hydrogenmethylsiloxane-co-dimethylsiloxane) crosslinker were mixed with a 2-roll mill and 60 parts of drug substance were added. The mixture was extruded through dies to desired dimensions (OD 1.6 mm) and crosslinked in an oven by heat. The cores were removed, cooled and cut to desired length (10 mm). The content of the drug was 60% (wt/wt) based on HPLC assay.

Implant Preparation 11 mm membranes were swelled with cyclohexane and cores were inserted. Cyclohexane was allowed to evaporate and ends were closed with a silicone adhesive. After 24 hours the ends were cut to give 0.5 mm end-caps.

Example 3

25% PEO-b-PDMS Membrane Preparation 24 parts of commercial poly(triethyleneoxide-b-deka (dimethylsiloxane))triethyleneoxide vinyl ether terminated, 74 parts silica-filled poly(dimethylsiloxane-co-vinylmethylsiloxane) and 10 ppm Pt-catalyst (of the reacting species) and 0.03 parts inhibitor (ethynyl cyclohexanol), approx. 2 parts of poly(hydrogenmethylsiloxane-co-dimethylsiloxane) crosslinker were mixed with a 2-roll mill. The mixture was extruded to a tube-like form with a wall thickness of 0.3 mm and cured by heat.

Core Preparation 19.7 parts of commercial poly(triethyleneoxide-b-deka (dimethylsiloxane))triethyleneoxide vinyl ether terminated, 19.7 parts poly(dimethylsiloxane-co-vinylmethylsiloxane) and 10 ppm Pt-catalyst (of the reacting species) and 0.02 parts inhibitor (ethynyl cyclohexanol), approx. 0.6 parts of poly(hydrogenmethylsiloxane-co-dimethylsiloxane) crosslinker were mixed with a 2-roll mill and 60 parts of drug substance were added. The mixture was extruded through dies to desired dimensions (OD 1.6 mm) and crosslinked in an oven by heat. The cores were removed, cooled and cut to desired length (10 mm). The content of the drug was 60% (wt/wt) based on HPLC assay.

Implant Preparation 11 mm membranes were swelled with cyclohexane and cores were inserted. Cyclohexane was allowed to evaporate and ends were closed with a silicone adhesive. After 24 hours the ends were cut to give 0.5 mm end-caps.

Example 4

20% PEO-b-PDMS Membrane Preparation 19 parts of commercial poly(triethyleneoxide-b-deka (dimethylsiloxane))triethyleneoxide vinyl ether terminated, 79 parts silica-filled poly(dimethylsiloxane-co-vinylmethylsiloxane) and 10 ppm Pt-catalyst (of the reacting species) and 0.03 parts inhibitor (ethynyl cyclohexanol), approx. 2 parts of poly(hydrogenmethylsiloxane-co-dimethylsiloxane) crosslinker were mixed with a 2-roll mill. The mixture was extruded to a tube-like form with a wall thickness of 0.3 mm and cured by heat.

Core Preparation 19.7 parts of commercial poly(triethyleneoxide-b-deka (dimethylsiloxane))triethyleneoxide vinyl ether terminated, 19.7 parts poly(dimethylsiloxane-co-vinylmethylsiloxane) and 10 ppm Pt-catalyst (of the reacting species) and 0.02 parts inhibitor (ethynyl cyclohexanol), approx. 0.6 parts of poly(hydrogenmethylsiloxane-co-dimethylsiloxane) crosslinker were mixed with a 2-roll mill and 60 parts of drug substance were added. The mixture was extruded through dies to desired dimensions (OD 1.6 mm) and crosslinked in an oven by heat. The cores were removed, cooled and cut to desired length (10 mm). The content of the drug was 60% (wt/wt) based on HPLC assay.

Implant Preparation 11 mm membranes were swelled with cyclohexane and cores were inserted. Cyclohexane was allowed to evaporate and ends were closed with a silicone adhesive. After 24 hours the ends were cut to give 0.5 mm end-caps.

Example 5

10% PEO-b-PDMS Membrane Preparation 9 parts of commercial poly(triethyleneoxide-b-deka(dimethylsiloxane))triethyleneoxide vinyl ether terminated, 89 parts silica-filled poly(dimethylsiloxane-co-vinylmethylsiloxane) and 10 ppm Pt-catalyst (of the reacting species) and 0.03 parts inhibitor (ethynyl cyclohexanol), approx. 2 parts of poly-(hydrogenmethylsiloxane-co-dimethylsiloxane) crosslinker were mixed with a 2-roll mill. The mixture was extruded to a tube-like form with a wall thickness of 0.3 mm and cured by heat.

Core Preparation 19.7 parts of commercial poly(triethyleneoxide-b-deka (dimethylsiloxane))triethyleneoxide vinyl ether terminated, 19.7 parts poly(dimethylsiloxane-co-vinylmethylsiloxane) and 10 ppm Pt-catalyst (of the reacting species) and 0.02 parts inhibitor (ethynyl cyclohexanol), approx. 0.6 parts of poly(hydrogenmethylsiloxane-co-dimethylsiloxane) crosslinker were mixed with a 2-roll mill and 60 parts of drug substance were added. The mixture was extruded through dies to desired dimensions (OD 1.6 mm) and crosslinked in an oven by heat. The cores were removed, cooled and cut to desired length (10 mm). The content of the drug was 60% (wt/wt) based on HPLC assay.

Implant Preparation 11 mm membranes were swelled with cyclohexane and cores were inserted. Cyclohexane was allowed to evaporate and ends were closed with a silicone adhesive. After 24 hours the ends were cut to give 0.5 mm end-caps.

Drug Release Tests

The release rates of the drug from the implants were measured in vitro as follows:

The implants were attached into a stainless steel holder in vertical position and the holders with the implants were placed into glass bottles containing 75 ml of a dissolution medium. The glass bottles were shaken in shaking waterbath 100 rpm at 37° C. The dissolution medium was withdrawn and replaced by a fresh dissolution medium at predetermined time intervals, and the released drug was analysed by HPLC. The concentration of the dissolution medium and the moment of change (withdrawal and replacement) of medium were selected so that sink-conditions were maintained during the test.

The results are illustrated in FIG. 6. FIG. 6 shows that the release rates are clearly dependent on the nature of the membrane. In FIG. 6, the losanges illustrate the results of Example 2, the squares illustrate the results of Example 3, the triangles illustrate the results of Example 4 and the stars illustrate the results of Example 5.

The invention claimed is:

1. A method for manufacturing an otorhinological delivery device, comprising preparing a core comprising at least one pharmaceutically active agent and an elastomer composition selected from the group consisting of poly(dimethylsiloxane), a siloxane-based elastomer comprising 3,3,3-trifluoropropyl groups attached to the Si-atoms of the siloxane units, a siloxane-based elastomer comprising poly (alkylene oxide) groups and mixtures thereof;

encasing said core with a membrane, said membrane being made of the same or a different elastomer composition than said core, said elastomer composition of said membrane being selected from said group, thereby forming an implantable device, shaping said implantable device into a shape suitable for implantation into the ear or nose of a human or animal, wherein the pharmaceutically active agent is selected from the group comprising dexamethasone, betamethasone, beclomethasone, budesonide and mixtures thereof.

2. The method of claim 1, wherein said elastomer composition comprises a siloxane-based elastomer comprising 3,3,3-trifluoropropyl groups attached to the Si-atoms of the siloxane units and wherein in said siloxane-based elastomer 1 to 49.5% of the substituents attached to the Si-atoms of the siloxane units are 3,3,3-trifluoropropyl groups.

3. The method of claim 1, wherein said elastomer composition comprises a siloxane-based elastomer comprising poly(alkylene oxide) groups and wherein said poly(alkylene oxide) groups are present as alkoxy-terminated grafts or blocks linked to the polysiloxane units by silicon-carbon bonds or as a mixture of these forms.

4. The method of claim 3, wherein said poly(alkylene oxide) groups are poly(ethylene oxide) groups.

5. The method of claim 1, wherein said membrane and said core are made of the same elastomer composition.

6. The method of claim 1, wherein said membrane and said core are made of different elastomer compositions.

7. The method of claim 1, wherein said device is an otological delivery device and wherein the elastomer composition comprises poly(dimethylsiloxane) and a siloxane-based elastomer comprising poly(ethylene oxide) groups.

8. A method of treatment of an otological disorder, comprising placing in the ear of a patient in need of said treatment an otorhinological delivery device prepared according to claim 1, wherein said otological disorder is selected from the group consisting of otitis, acute infections, cochlear and vestibular disorders, vertigo, Meniere's disease, sudden deafness, sensoneurinal hearing loss, tinnitus, motion sickness, endolymphatic hydrops, endolymphatic hypertension, perilymphatic hypertension, perilymphatic hydrops, perilymphatic fistula, intracochlear fistula and ruptures in various membrane structures within the ear.

9. A method of treatment of a nasal disorder, comprising placing in the nose of a patient in need of said treatment an otorhinological delivery device prepared according to claim 1, wherein said nasal disorder is selected from the group consisting of nasal inflammatory disorders, allergic reactions, asthma and fungal infections.

* * * * *